US011911588B2

(12) United States Patent
Chen et al.

(10) Patent No.: US 11,911,588 B2
(45) Date of Patent: Feb. 27, 2024

(54) SYRINGE

(71) Applicant: MicroVention, Inc., Aliso Viejo, CA (US)

(72) Inventors: Samuel Chen, Lake Forest, CA (US); Steve Trom, Costa Mesa, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 493 days.

(21) Appl. No.: 16/986,129

(22) Filed: Aug. 5, 2020

(65) Prior Publication Data

US 2021/0038803 A1 Feb. 11, 2021

Related U.S. Application Data

(60) Provisional application No. 62/883,472, filed on Aug. 6, 2019.

(51) Int. Cl.
*A61M 5/00* (2006.01)
*A61M 5/31* (2006.01)
(Continued)

(52) U.S. Cl.
CPC ......... *A61M 5/007* (2013.01); *A61K 49/0404* (2013.01); *A61M 5/31* (2013.01);
(Continued)

(58) Field of Classification Search
CPC .. A61M 2005/3104; A61M 2005/3106; A61M 5/31596; A61M 5/002; A61M 5/31;
(Continued)

(56) References Cited

U.S. PATENT DOCUMENTS 2,677,374 A * 5/1954 Burnside ................. A61M 5/28
604/199
3,543,967 A * 12/1970 O'Connor ............. A61M 5/284
222/386

(Continued)

FOREIGN PATENT DOCUMENTS

EP 0022576 A1 * 1/1981 ............. A61M 5/34
JP 3040594 U 8/1997
(Continued)

OTHER PUBLICATIONS

English translation of Masaomi et al. (WO-2014045336-A1) (Year: 2022).*

(Continued)

*Primary Examiner* — Nilay J Shah
(74) *Attorney, Agent, or Firm* — K&L Gates LLP; Brian J. Novak; Giorgios N. Kefallinos

(57) ABSTRACT

Described herein are syringe caps including a plug portion and a protruding member extending from one end of the plug portion. The protruding member can extend a length greater than a depth of an accumulated component in the syringe. Also described herein, are systems including a syringe containing a composition and a syringe cap. The syringe cap can include a luer-lock with a projecting member that projects into the syringe. The projecting member can assist in creating a tunnel through the accumulated material thereby allowing degassing of the composition. The projecting member can also help to prevent accumulation of a radiopaque visualization agent or contrast agent that may accumulate along one end of the syringe.

24 Claims, 8 Drawing Sheets

(51) Int. Cl.
 *A61K 49/04* (2006.01)
 *A61M 5/315* (2006.01)
(52) U.S. Cl.
 CPC ......... *A61M 5/002* (2013.01); *A61M 5/31596* (2013.01); *A61M 2005/3104* (2013.01); *A61M 2005/3106* (2013.01); *A61M 2202/0468* (2013.01)
(58) Field of Classification Search
 CPC .......... A61M 2202/0468; A61M 5/007; A61M 2202/06; A61M 2202/064
 See application file for complete search history.

(56) References Cited

U.S. PATENT DOCUMENTS

| | | | | |
|---|---|---|---|---|
| 3,927,762 | A * | 12/1975 | Zdarsky | B65D 75/28 |
| | | | | 206/229 |
| 4,185,628 | A * | 1/1980 | Kopfer | A61M 5/284 |
| | | | | 604/82 |
| 4,390,016 | A * | 6/1983 | Riess | A61M 5/002 |
| | | | | 604/236 |
| 5,531,710 | A * | 7/1996 | Dang | A61M 5/178 |
| | | | | 222/546 |
| 5,624,402 | A * | 4/1997 | Imbert | A61M 5/3134 |
| | | | | 604/533 |
| 5,779,668 | A * | 7/1998 | Grabenkort | A61M 5/3129 |
| | | | | 604/218 |
| 5,807,345 | A * | 9/1998 | Grabenkort | A61M 5/3134 |
| | | | | 604/199 |
| 6,068,614 | A * | 5/2000 | Kimber | A61M 5/315 |
| | | | | 604/238 |
| 6,196,998 | B1 * | 3/2001 | Jansen | A61M 5/3134 |
| | | | | 604/111 |
| 6,440,101 | B1 * | 8/2002 | Grabenkort | A61M 5/31596 |
| | | | | 604/82 |
| 6,632,199 | B1 * | 10/2003 | Tucker | A61M 5/3134 |
| | | | | 604/192 |
| 7,041,087 | B2 * | 5/2006 | Henderson | A61M 5/345 |
| | | | | 604/200 |
| 7,883,490 | B2 * | 2/2011 | Casey, II | A61M 5/284 |
| | | | | 604/82 |
| 9,108,031 | B2 | 8/2015 | Brandenburger et al. | |
| 2007/0129630 | A1 * | 6/2007 | Shimko | A61B 90/36 |
| | | | | 600/431 |
| 2010/0059702 | A1 | 3/2010 | Mansour et al. | |
| 2018/0126081 | A1 | 5/2018 | Glocker et al. | |
| 2019/0175734 | A1 | 6/2019 | D'Agostino et al. | |

FOREIGN PATENT DOCUMENTS

| | | | | |
|---|---|---|---|---|
| WO | WO-2014045336 A1 * | 3/2014 | ............ | A61M 5/002 |
| WO | 2021/026269 A1 | 2/2021 | | |

OTHER PUBLICATIONS

International Search Report and Written Opinion, dated Oct. 22, 2020, for International Application No. PCT/US2020/045061 filed on Aug. 5, 2020.

* cited by examiner

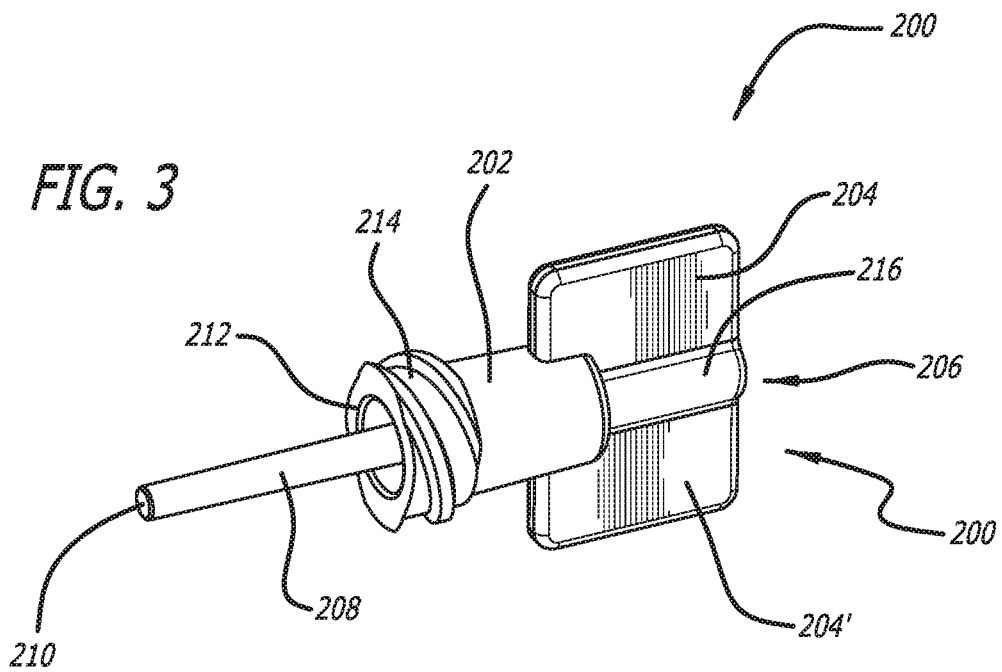
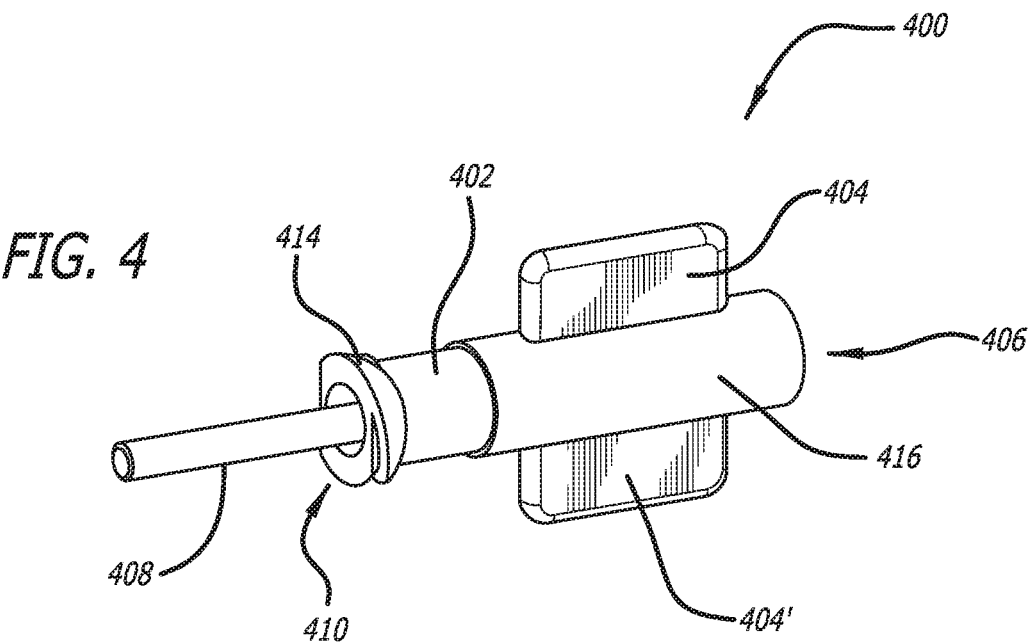

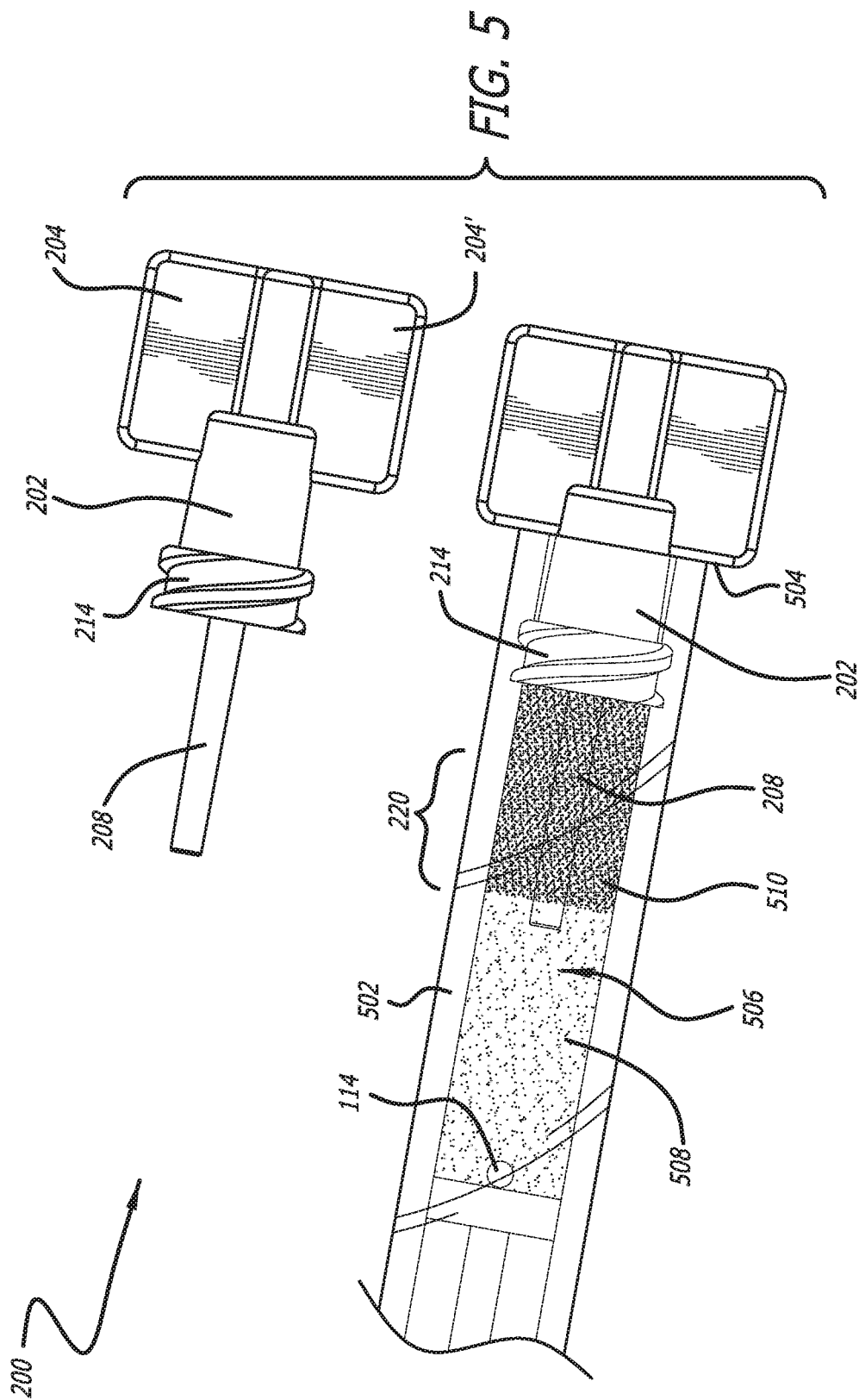

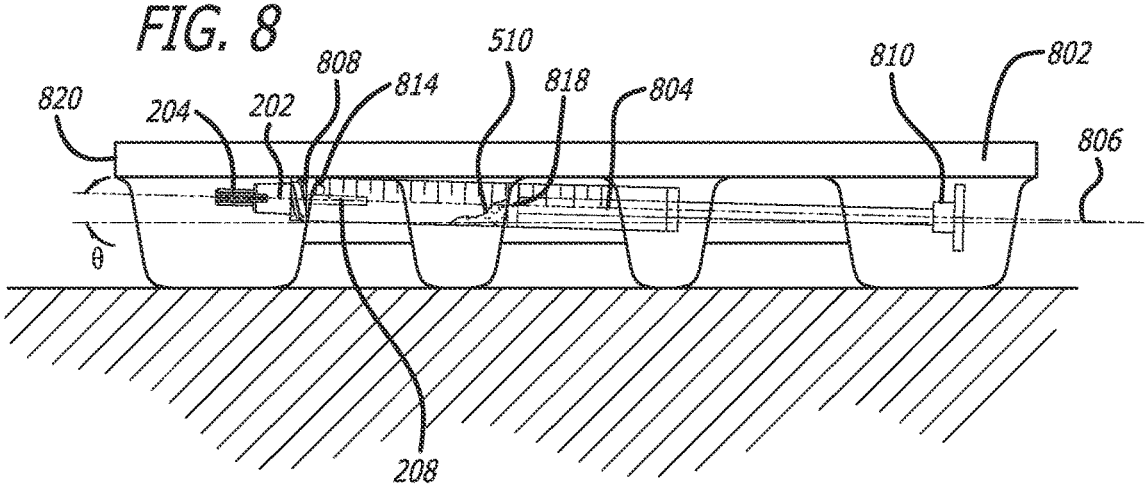
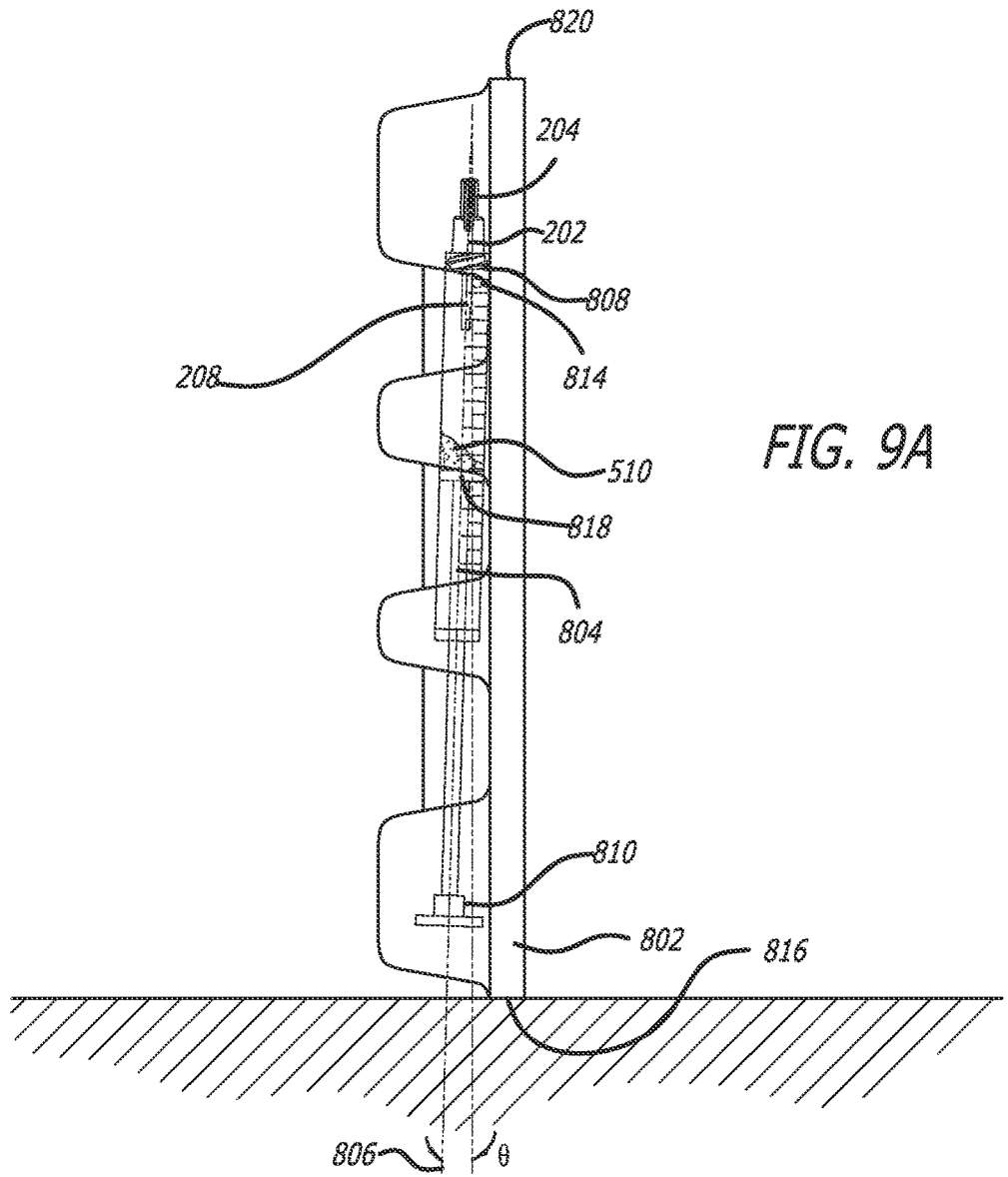

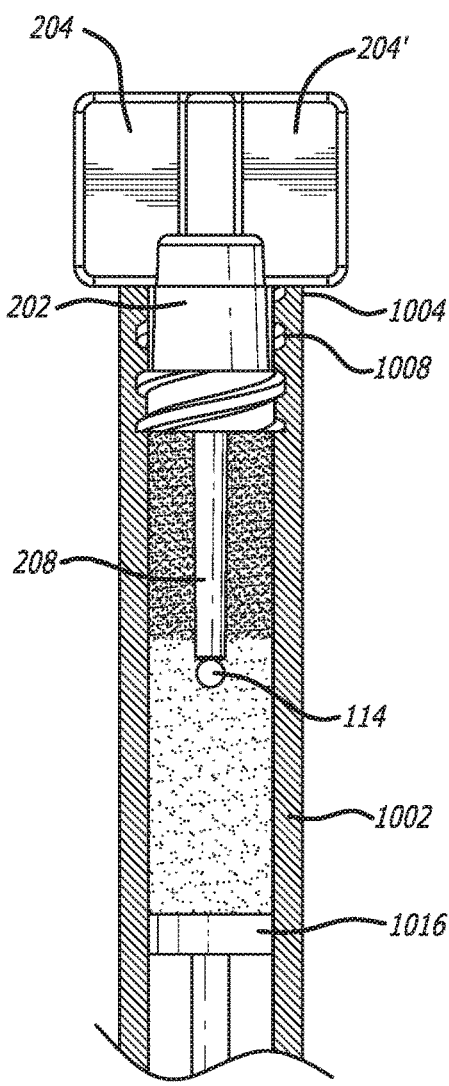
FIG. 10
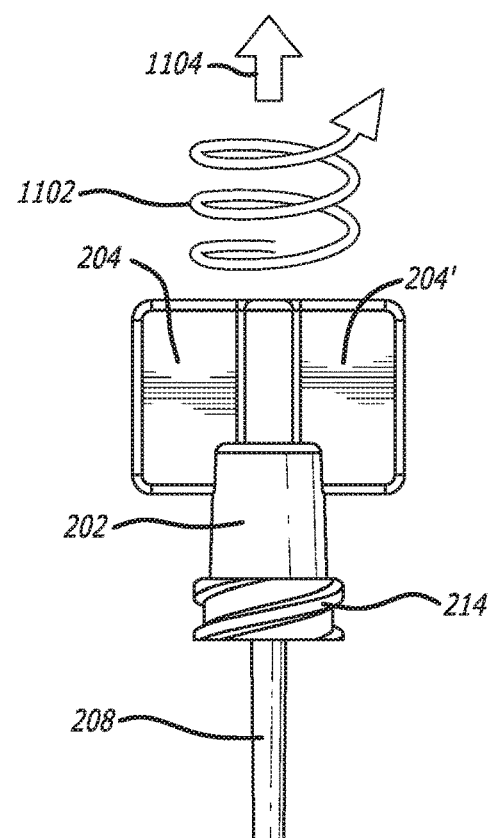
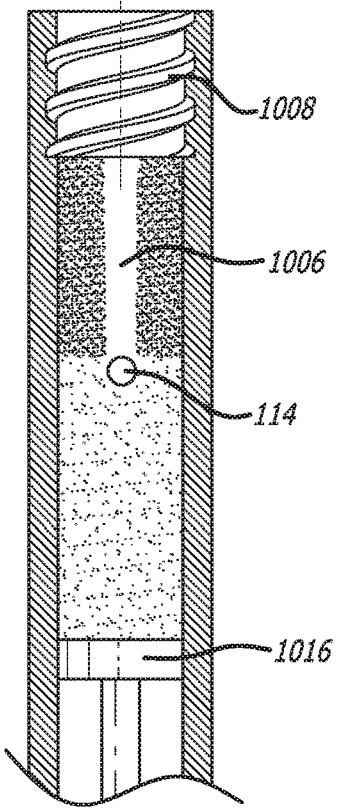
FIG. 11

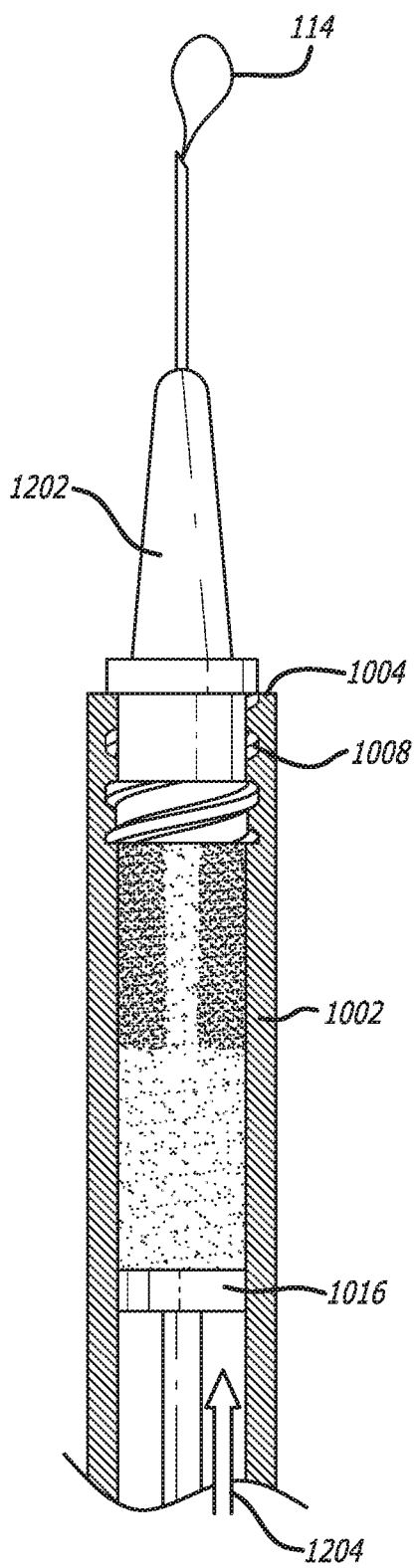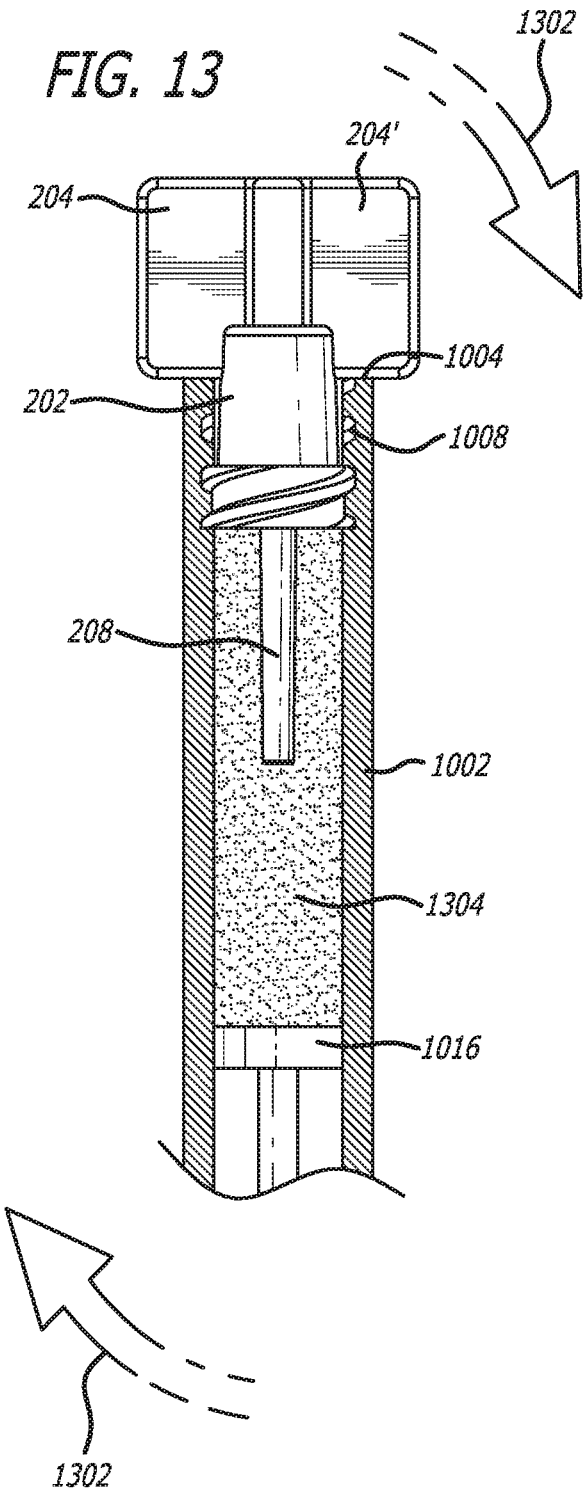

SYRINGE

CROSS REFERENCE TO RELATED APPLICATIONS

This application claims the benefit of U.S. Provisional Patent Application No. 62/883,472, filed Aug. 6, 2019, the entire disclosures of which is incorporated herein by reference.

BACKGROUND

Liquid embolics are part of a newer class of occlusive products designed to treat complications in the vasculature. One particular area where liquid embolics offer benefit is in the treatment of arteriovenous malformations (AVM), which involve a tangled mass of abnormal blood vessels which often develop in the brain, affecting the normal flow of blood. The liquid embolic hardens or solidifies after delivery, thereby occluding the target treatment area.

To aid in imaging the embolic material after injection, the liquid embolic can include a radiopaque agent. The radiopaque agent can be molecularly attached to the embolic compound, or it can comprise a separate compound that is suspended in the embolic solution. In the latter case, the typical delivery procedure involves agitating a bottle of the liquid embolic to suspend the separate radiopaque agent, then filling a syringe with the liquid embolic, and delivering the contents of the syringe to the patient vasculature.

A better delivery solution would involve the use of a pre-filled syringe provided to the user to eliminate the need for a syringe filling step. However, until now this is not possible since the radiopaque agent will settle toward the lowest part of the syringe during shipping and storage, creating a fixed accumulated mass over time, which makes it difficult to degas and mix the composition later.

To avoid these complications, there is a need for a syringe system that prevents these issues, thereby making a pre-filled liquid embolic syringe possible.

SUMMARY

In some embodiments, a system including a syringe containing a composition, for example a liquid-embolic composition, and syringe cap is described. The syringe cap can include a luer-lock with a projecting member that projects into the syringe. The projecting member can assist in creating a tunnel through the accumulated material thereby allowing degassing of the composition. The projecting member can also help to prevent accumulation of radiopaque visualization, agent or contrast agent, that may accumulate along one end of the syringe.

In other embodiments, a syringe cap including a locking mechanism used to cap an end of a syringe is described. The syringe cap can include a projecting member that projects axially or longitudinally into the syringe, thereby helping to prevent accumulation of radiopaque visualization agent along one end of the syringe and allowing for degassing of the stored composition.

Further described are syringe caps that include a plug portion having a first end and a second end, wherein the plug portion is configured to attach to a delivery end of a syringe, and a protruding member extending from the second end of the plug portion at least 2 mm.

In some embodiments, the protruding member extends at least 5 mm or at least 10 mm.

In some embodiments, the protruding member has a cross-sectional shape selected from circular, elliptical, square, triangular, pentagonal, hexagonal, heptagonal, octagonal, torx, or star.

In some embodiments, the protruding member has a pointed or sharp second end.

In other embodiments, the syringe cap further includes a device capable of securing the syringe cap to the syringe. This device can be a luer connector or a friction connector.

Systems for degassing a composition in a syringe are also described. The systems can include a syringe including a connection at its delivery end; a syringe cap including a plug portion having a first end and a second end, wherein the plug portion is configured to attach to the connection and a protruding member extending from the second end of the plug portion; and a composition in the syringe that includes a first component and a second component, wherein the second component accumulates when the syringe is stored.

In some embodiments, the first component is a therapeutic composition and/or the second component is a visualization agent. In some embodiments, the first component is simply a carrier or solvent for the second component.

The visualization agent can be configured to allow the composition to be viewed by fluoroscopy, computed tomography, or magnetic resonant imaging.

The visualization agent can include barium, bismuth, tantalum, platinum, gold, iodine, iron oxide, gadolinium, or a combination thereof. In some embodiments, the visualization agent is barium sulfate.

In some embodiments, the protruding member extends a length greater than a depth of the second component when accumulated. In other embodiments, the protruding member is configured to create a tunnel through the second component when accumulated.

Methods of degassing a composition in a syringe having accumulated material over the delivery end of a syringe are also described. These methods can include removing gas, e.g., bubble(s) from a composition within the syringe after removing a syringe cap including a protruding member that extends axially, or longitudinally, into the syringe and through the accumulated material thereby forming a tunnel through the accumulated material.

In some embodiments, the accumulated material is a visualization agent.

In other embodiments, the syringe cap further includes a plug portion having a first end and a second end, wherein the plug portion is configured to attach to the delivery end of the syringe.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 3 illustrates another view of the syringe cap illustrated in FIG. 2.

FIG. 4 illustrates an alternative design of a syringe cap as described herein.

FIG. 5. illustrates a syringe cap as described herein attached to a syringe including a composition including a first component and a second component.

FIG. 8 illustrates syringes including syringe caps stored horizontally at an angle.

FIG. 9A illustrates syringes including syringe caps stored vertically, right side up, at an angle.

FIG. 10 illustrates a syringe cap installed and ready to use.

FIG. 11 illustrates removal of a syringe cap to present a tunnel through the second component for degassing.

FIG. 12 illustrates degassing.

FIG. 13 illustrates recapping and mixing of the first component and the second component after degassing.

DESCRIPTION OF EMBODIMENTS

Described herein are syringe caps that include a protruding member that projects axially, or longitudinally, into a syringe barrel once attached to a delivery or injection end of a syringe.

With the inclusion of a syringe cap as described herein, including a protruding member, it is possible to make a pre-filled syringe which can be shipped to an end user for use in a therapeutic procedure, such as occlusion of an AVM.

Figure 1:
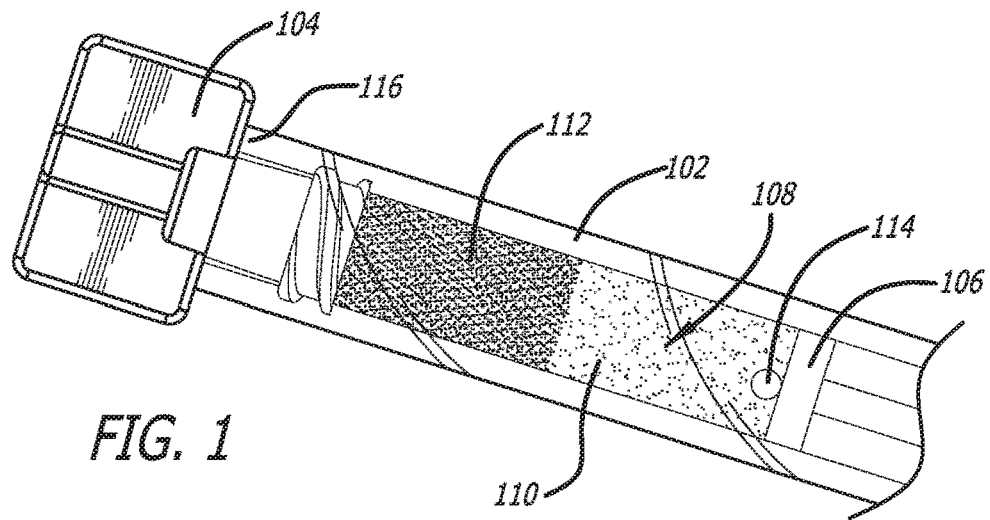
FIG. 1 shows a conventional syringe with radiopaque agent accumulated at one end thereof.

Conventional medications or diagnostic formulations delivered from a manufacturer in pre-filled syringes are often similar to those of FIG. 1. These include syringe body 102, cap 104, and plunger 106, wherein formulation 108 is included in syringe body 102. Often, formulation 108 can include two or more components such as first component 110 and second component 112. In some embodiments, first component 110 and second component 112 may separate during shipping and/or require mixing prior to delivery. In some embodiments, as described herein, first component 110 can be a carrier and/or a medicament and/or a therapeutic component and second component 112 can be a diagnostic component.

In some embodiments, the medicament or therapeutic component can be a drug solution, a solution including micro- or nano-particles, an embolic solution, a filler solution, or a combination thereof. In some embodiments, the medicament or therapeutic component can have a low enough viscosity that it can flow freely out of a conventional needle or catheter.

In some embodiments, the first component is a carrier or other liquid component. Carriers can include pharmaceutically acceptable materials and/or compositions, such as a liquid or solid fillers, stabilizers, dispersing agents, suspending agents, diluent, excipients, thickening agents, solvents or encapsulating materials, involved in carrying or transporting a first component, a second component, or a combination of a first component and a second component. Carriers can be acceptable in the sense of being compatible with the other ingredients of the formulation, and not injurious to a patient.

Carriers can include, but are not limited to water, saline, aqueous dextrose, glycerol, ethanol and the like; solubilizing agents and emulsifiers, such as, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances.

Other additional ingredients that may be included in the formulations as a first or second component may be known in the art and described, for example in Remington's Pharmaceutical Sciences (Genaro, Ed., Mack Publishing Co., 1985, Easton, Pa.), which is incorporated herein by reference.

In some embodiments, the diagnostic component can be a visualization agent. In some embodiments, a visualization agent can also be referred to as a contrast agent. Visualization agents can be used to allow medically relevant imaging techniques such as fluoroscopy, computed tomography, or magnetic resonant imaging.

Visualization under fluoroscopy can be imparted by the incorporation of solid particles of radiopaque materials such as barium, bismuth, tantalum, platinum, gold, and other dense metals or by the incorporation of iodine-containing molecules often onto or into a polymer. Visualization agents for fluoroscopy can be barium sulfate and iodine-containing molecules.

Visualization under computed tomography imaging can be imparted by incorporation of solid particles of barium or bismuth or by the incorporation of iodine-containing molecules. Often the agents useful for computed tomography can be barium sulfate and iodine-containing molecules.

Visualization under magnetic resonance imaging can be imparted by the incorporation of solid particles of superparamagnetic iron oxide or gadolinium molecules.

In some embodiments, a formulation housed in a syringe as described herein can be a liquid embolic composition. A commercially available liquid embolic composition which includes a visualization agent is known as Onyx, and is described in U.S. Pat. No. 6,756,031, which is hereby incorporated by reference in its entirety. Another such liquid embolic composition which utilizes a suspended visualization agent is described in U.S. Pat. No. 9,351,993, which is hereby incorporated by reference in its entirety.

In some embodiments, when the liquid embolic composition is Onyx, the composition can include a polymer selected from polyacrylonitrile, polyurethane, polyvinylacetate, cellulose acetate butyrate, nitrocellulose and copolymers of urethane/carbonate and copolymers of styrene/maleic add and a visualization agent selected from metrizamide, iopamidol, iothalamate sodium, iodomide sodium, meglumine, tantalum, tantalum oxide, barium sulfate, gold, tungsten, and platinum.

In some embodiments, the liquid embolic composition includes a polymer including a first monomer selected from aminopropyl methacrylamide, aminoethyl methacrylamide, N-(3-methylphridine)acrylamide, N-(2-(4-aminophenyl) ethylacrylamide, N-(4-aminobenzyl)acrylamide, N-(2-4-imidazolyl)ethyl)acrylamide and combinations thereof, a second monomer selected from t-butyl acrylate, t-butyl acrylamide, n-octyl methacrylate, methyl methacrylate, hydroxyethyl methacrylate, hydroxyethyl acrylate, hydroxypropyl methacrylate, hydroxybutyl methacrylate, hydroxybutyl acrylate, n-octyl acrylate, methyl acrylate, hydroxyethyl acrylate, hydroxypropyl acrylate, derivatives thereof or combinations thereof, and a visualization agent selected from an iodinated compound, barium sulfate, tantalum, superparamagnetic iron oxide, gadolinium molecules or a combination thereof.

In some embodiments, the liquid embolic compositions can be aqueous or non-aqueous. In some embodiments, the liquid embolic can be organic.

In some embodiments, the liquid embolic includes a visualization agent that is polymerized into the embolic polymer and then degrades from the polymer after delivery.

In some embodiments, the liquid embolic compositions can be an insoluble polymer when delivered. In other embodiments, the liquid embolic compositions can be soluble in the aqueous solution and insoluble at a physiological pH at a treatment site once delivered. In some embodiments, the polymers in the liquid embolics may not polymerize until they are delivered. In some embodiments, polymerization in situ can be using light.

In some embodiments, the liquid embolic can precipitate when coming in contact with blood or other physiological fluid. If the pH of the physiological fluid is the solubility trigger, the physiological pH can be a pH of about 7.0, about 7.1, about 7.2, about 7.3, about 7.4, about 7.5, about 7.6, about 7.7 or about 7.8, between about 7.0 and about 7.8, between about 7.1 and about 7.7, between about 7.2 and about 7.6, or any value in a range bound by or between any of these values. The non-physiological pH can be a pH between about 1.0 and about 6.9, or about 2.0 and about 6.0, about 7.9 and about 12.0, about 8.5 and about 10.0. Alternatively, if the solubility trigger is solubility in a water miscible organic solvent and insolubility at physiological conditions, any physiological environment can initiate the precipitation.

In some embodiments, a liquid emboilic polymer can include a reaction product of a first monomer such as, but not limited to, hydroxyethyl methacrylate, hydroxyethyl methacrylamide, t-butyl acrylate, t-butyl acrylamide, n-octyl methacrylate, methyl methacrylate, other acrylates, methacrylates, acrylamides, methacrylamides, vinyl containing compounds, and combinations thereof and at least one second monomer that includes a visualization agent attached thereto, such as Iodine. Second monomers that include a visualization agent attached thereto can include, but are not limited to triiodophenol, 2-oxo-2-(1-oxo-1-(1-oxo-1-(2,4,6-triiodophenoxy)propan-2-yloxy)propan-2-yloxy)ethoxy) ethyl acrylate, 1-((2-(methacryloyloxy)ethoxy)carbonyloxy) ethyl 3,5-diacetamido-2,4,6-triiodobenzoate, and combinations thereof.

In one embodiment described herein, the liquid embolic polymer comprises a reaction product of 2-oxo-2-(1-oxo-1-(1-oxo-1-(2,4,6-triiodophenoxy)propan-2-yloxy)propan-2-yloxy)ethoxy)ethyl acrylate, hydroxyethyl methacrylate, and azobisisobutyronitrile. In another embodiment, the liquid embolic polymer comprises a reaction product of between about 75% and about 98% 2-oxo-2-(1-oxo-1-(1-oxo-1-(2,4,6-triiodophenoxy)propan-2-yloxy)propan-2-yloxy)ethoxy)ethyl acrylate, between about 2% and about 25% hydroxyethyl methacrylate, and less than about 1% azobisisobutyronitrile. In still another embodiment, the liquid embolic polymer comprises a reaction product of between about 85% and about 98% 2-oxo-2-(1-oxo-1-(1-oxo-1-(2,4,6-triiodophenoxy)propan-2-yloxy)propan-2-yloxy)ethoxy)ethyl acrylate, between about 2% and about 15% hydroxyethyl methacrylate, and less than about 1% azobisisobutyronitrile.

In another embodiment described herein, the liquid embolic polymer comprises a reaction product of 1-((2-(methacryloyloxy)ethoxy)carbonyloxy) ethyl 3,5-diacetamido-2,4,6-triiodobenzoate, hydroxyethyl methacrylate, and azobisisobutyronitrile. In another embodiment, the liquid embolic polymer comprises a reaction product of between about 85% and about 98% 1-((2-(methacryloyloxy)ethoxy)carbonyloxy) ethyl 3,5-diacetamido-2,4,6-triiodobenzoate, between about 2% and about 15% hydroxyethyl methacrylate, and less than about 1% azobisisobutyronitrile.

In still another embodiment described herein, the liquid embolic polymer comprises a reaction product of 1-((2-(methacryloyloxy)ethoxy)carbonyloxy) ethyl 3,5-diacetamido-2,4,6-triiodobenzoate, N-(3-Aminopropyl)methacrylamide hydrochloride, and azobisisobutyronitrile. In another embodiment, the liquid embolic polymer comprises a reaction product of about 74% 1-((2-(methacryloyloxy)ethoxy) carbonyloxy) ethyl 3,5-diacetamido-2,4,6-triiodobenzoate, about 26% N-(3-Aminopropyl)methacrylamide hydrochloride, and less than about 1% azobisisobutyronitrile.

In one embodiment, the liquid embolic can include a substantially stable biocompatible polymer comprising a reaction product of: a first monomer including a polymerizable moiety having a biodegradable linkage to a visualization agent having at least one aromatic ring, wherein the at least one aromatic ring includes a plurality of iodine atoms, and a second monomer including a polymerizable moiety and at least one hydroxyl group.

These liquid embolics are typically shipped in a separate container from the visualization agent. Both are then mixed prior to the procedure by a mechanical agitator in order to suspend the visualization agent within the liquid embolic, thereby forming a mixture. Once this is done, the embolic with the suspended visualization agent is then poured or pulled into a syringe, and the syringe is used to deliver the embolic into a patient's vasculature or other void. This is a laborious and time-consuming procedure.

A more convenient procedure is to utilize a pre-filled syringe which is shipped to the end user. The pre-filled syringe can be agitated on-site to suspend the visualization agent. However, up until now this has not been possible. One reason is that the visualization agent can settle to the bottom of the syringe during shipment and storage thereby creating a homogenous, accumulated mass over time. This essentially renders the syringe useless since the settled radiopaque agent clogs one end of the syringe, making further use (including degassing and mixing the syringe, and/or expelling the contents of the syringe) difficult, or even impossible.

This can result in a configuration illustrated in FIG. 1, wherein second component 112 accumulates around delivery end 116 of syringe body 102, meaning the end of the syringe body 102 where an embolic delivery takes place during a procedure. In some embodiments, this accumulation can result in a complete blockage of delivery end 116.

Further, many times, formulation 108 can also include an air bubble(s) 114 that needs to be degassed prior to delivery in order to remove bubble(s) 114 and/or any other bubbles that might be present. In some embodiments, if a blockage can be removed using shaking or vortexing, but bubble(s) 114 are not removed prior to shaking or vortexing, the bubbles can foam in the resulting mixing thereby making delivery of the composition impossible because bubbles and/or foam cannot be delivered directly to the vasculature as this would be dangerous. Further, foaming can lead to a thickening of the formulation, thereby affecting its delivery from syringe body 102 and further affecting the physical structure of formulation 108. These and other issues with formulations including multiple components are addressed herein.

Figure 2:
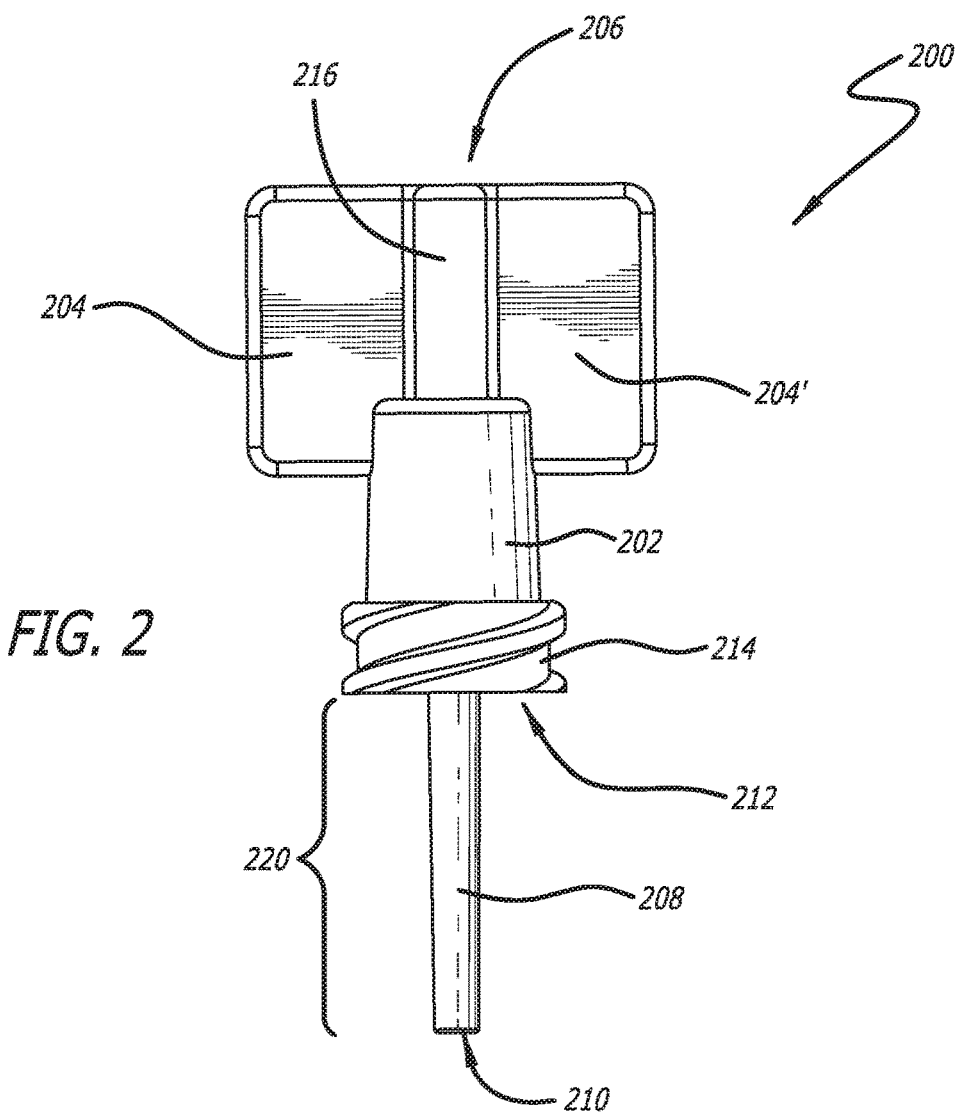
FIG. 2 illustrates a syringe cap as described herein with a protruding member emanating from one end thereof.

In some embodiments as illustrated in FIGS. 2 and 3, syringe cap 200 includes plug portion 202, gripping portions 204, 204' at first end 206, and protruding member 208 at second end 210.

Plug portion 202 can have any shape. In some embodiments, plug portion 202 has a generally cylindrical shape or a conical shape as illustrated in FIGS. 2 and 3. However, in other embodiments, the plug portion can have shapes with circular, elliptical, square, triangular, pentagonal, hexagonal, heptagonal, octagonal, torx, star, or other rectilinear shaped cross-sections.

The interior of the plug portion can be hollow or filled in with material.

An alternate configuration for a syringe cap is illustrated in FIG. 4. Syringe cap 400 includes plug portion 402, gripping portions 404, 404' near first end 406, and protruding member 408 at second end 410. Syringe cap also includes luer thread 414. As illustrated, gripping portions 404, 404' have a more axially rectangular shape than gripping portions 204, 204' of FIGS. 2-3.

In some embodiments, end 212 of plug portion 202 can include a mechanism to secure syringe cap 200 to a syringe body. In the embodiment illustrated in FIGS. 2 and 3, luer thread 214 is the securing mechanism. Luer thread 214 includes one or more threaded portions that rotatably mate with a syringe, generally in a male-female relationship where the threaded portions take on the male role in engaging the larger bore of the female syringe end. However, this configuration can also be flipped where the luer cap is a female receiving surface that accommodates a male projecting surface from the syringe end. In other embodiments, the securing mechanism can be a friction fit component, a snap fit, a snap, or the like—in lieu of a threaded mechanism.

In some embodiments, luer thread 214 can have various sizes. For example, as illustrated in FIG. 3, luer thread 214 is longer than luer thread 414 in FIG. 4. A longer luer thread can assist in achieving leak prevention when a syringe cap is attached to a syringe. However, a longer luer thread can also be more difficult to engage and disengage.

Gripping portions 204, 204' can have any shape that allows a user to grip and remove syringe cap through rotation or force. In one embodiment, gripping portions have generally rectangular shapes as illustrated in FIGS. 2 and 3. However, in other embodiments, gripping portions can have circular, elliptical, square, triangular, pentagonal, hexagonal, heptagonal, octagonal, torx, star, or other rectilinear shapes or portions.

In some embodiments, gripping portions can include texture to assist in gripping. Texture can be any material or configuration that assists in gripping and can cover all or any portion of a gripping surface. In some embodiments, texture can be a coating. In other embodiments, texture can be addition or elimination of gripping surface material. For example, stippled or granulated texture can be used in some embodiments. In other embodiments, stripped texture can be used. Coatings can include a polymer such as, but not limited to, rubber.

In some embodiments, gripping portions may include interface 216. Interface 216 can have any shape that allows gripping portions to be securely connected to plug portion 202. In one embodiment, interface 216 has a generally cylindrical shape or a conical shape as illustrated in FIGS. 2 and 3. However, in other embodiments, the interface can have shapes with circular, elliptical, square, triangular, pentagonal, hexagonal, heptagonal, octagonal, torx, star, or other rectilinear shaped cross-sections.

In some embodiments (e.g., as shown in FIG. 4) interface 416 has an axial length that is longer than gripping portions 404, 404'. In other words, interface 416 extends beyond proximal and distal ends of gripping portions 404, 404'.

In some embodiments, interface 216 is not included and gripping portions are directly connected to one another as a single unit. In some embodiments, interface 216 can add strength to gripping portions when a torque or other force is applied to the gripping portions.

In some embodiments, gripping portions need not be used. In such an embodiment, a user can apply force directly to plug portion 202.

Protruding member 208 can be connected to plug portion 202 at second end 212. In some embodiments, protruding member 208 can begin at second end. In other embodiments, protruding member 208 can begin at a location proximal to second end 212 (e.g., within a passage of plug portion 202).

The syringe cap fitting diameter as well as the protruding member width and length can be customized depending on the syringe size. For instance, depending on the volume of the housed composition, a volumetric component of the second component can be ascertained, and this can correspond to a particular volumetric dimension by itself. The second component, when settled in the syringe, can comprise this particular dimension, so that a protrusion member length can be used which can extend beyond this.

Figure 6:
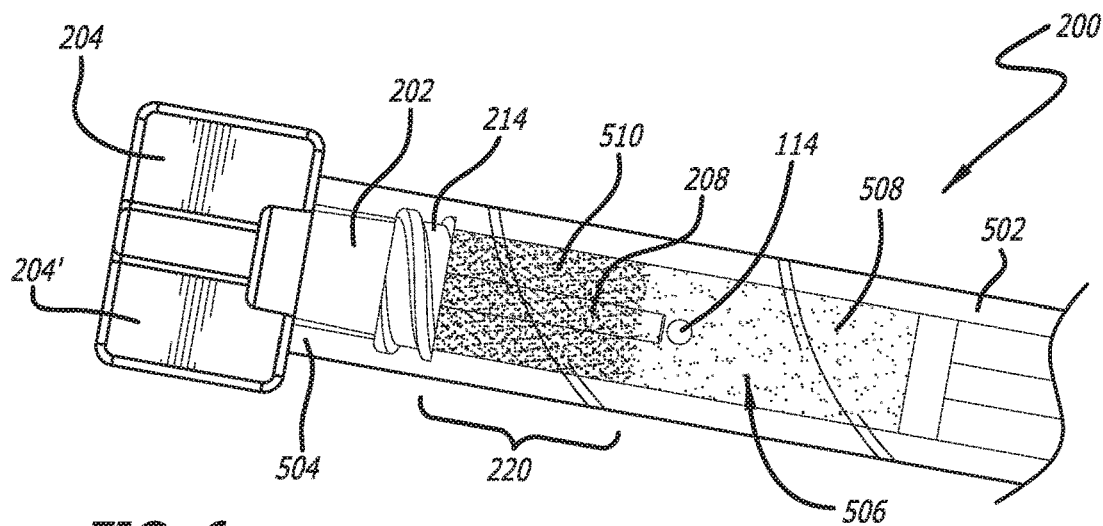
FIG. 6. illustrates another view of a syringe cap as described herein attached to a syringe including a composition including a first component and a second component.

Protruding member 208 can have a length 220, shown in FIGS. 2 and 6. Length 220 can be at least long enough to traverse the volume of an accumulating or accumulated component that is housed within a syringe. Length 220 can be greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, greater than about 10 mm, greater than about 11 mm, greater than about 12 mm, greater than about 13 mm, greater than about 14 mm, greater than about 15 mm, greater than about 16 mm, greater than about 17 mm, greater than about 18 mm, greater than about 19 mm, greater than about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm.

FIGS. 5 and 6 illustrate syringe cap 200 attached to a syringe 502. As seen, protruding member 208 projects axially, or longitudinally, into the luer end 504 of syringe 502 (which is also the delivery end of syringe 502). In some embodiments, a protruding member 208 can create a channel in an accumulated second component that has settled in the syringe around the protruding member. In other embodiments, a protruding member can help to prevent the component from accumulating and forming a clumped mass near the luer or delivery end of the syringe.

Protruding member 208, 408 can be an elongated member that traverses into a syringe barrel onto which syringe cap 200, 400 is attached. Protruding member 208, 408 can have any shape. In one embodiment, a protruding member has a generally cylindrical shape or a conical shape. However, in other embodiments, a protruding member can have shapes with circular, elliptical, square, triangular, pentagonal, hexagonal, heptagonal, octagonal, torx, star, or other rectilinear shaped cross-sections.

The syringe cap as described herein can be composed of any material that is not susceptible to moisture permeability since it is undesirable for moisture, liquids, or aqueous content to enter a sealed syringe. In some embodiments, the syringe cap is composed of plastic or other formable polymer material. In some embodiments, the plastic is an injection molded plastic. One particular example of such a material is COP plastic, one specific example is 690R COP plastic. However, in other embodiments, the syringe cap can be formed of a metal or metal alloy optionally including a plastic or polymer.

In some embodiments, the protruding member is formed from a different material than the remainder of syringe cap as described herein. In other embodiments, each component of the syringe cap, such as the protruding member, gripping portions, plug portion, etc. can be formed from a different material.

The material used to form the syringe cap can be able to handle sterilization since the syringes can be sterilized to make them safe to ship to an end user. Sterilization can include any common sterilization technique that does not substantially degrade the syringe cap, syringe, or composition. The sterilization method can be steam sterilization, autoclaving, gamma radiation, or ethylene oxide. The devices/components can be sterilized before or after packaging.

Figure 7:
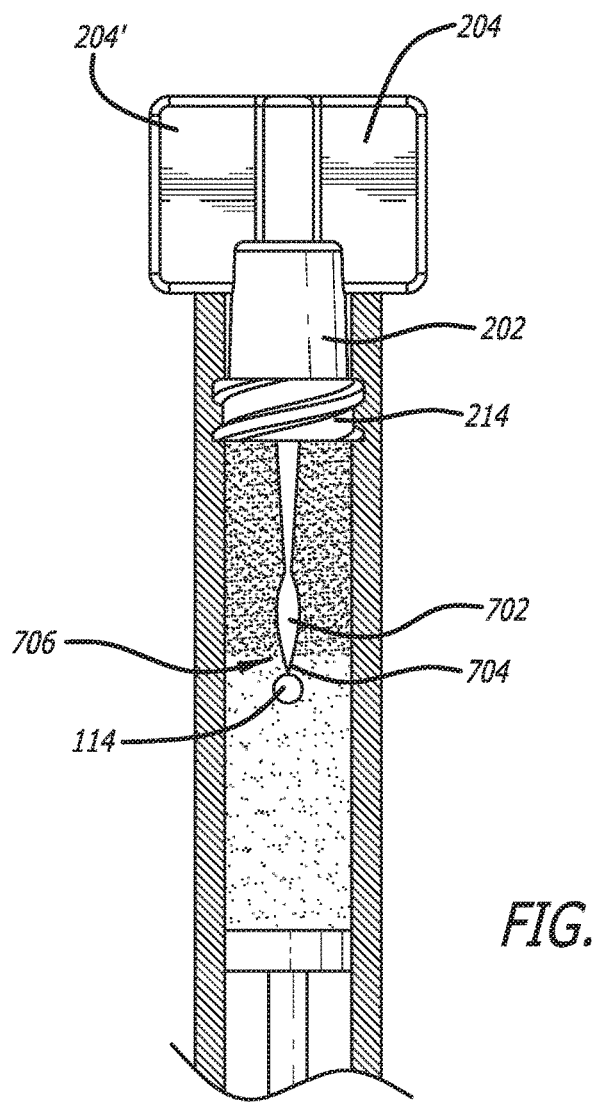
FIG. 7. illustrates another view of a syringe cap as described herein including an alternative protruding member attached to a syringe including a composition including a first component and a second component.

In some embodiments, does not substantially degrade can be used to indicate that after sterilization, at least, about 70%, about 80%, about 90%, about 95%, about 99%, or about 100% of the housed composition remains intact. In other embodiments, does not substantially degrade can be used to indicate that after sterilization, at least, about 70%, about 80%, about 90%, about 95%, about 99%, or about 100% of the syringe remains intact. In other embodiments, does not substantially degrade can be used to indicate that after sterilization, at least, about 70%, about 80%, about 90%, about 95%, about 99%, or about 100% of the syringe cap as described herein remains intact In one embodiment as illustrated in FIG. 7, protruding member 702 includes a point 704 at protruding member end 706. Further, the body of protruding member 702 can have any shape that can accommodate point 704 such as, but not limited to a cylinder, a cone, a spear, a spade, a lance, a pin, a nail, a screw, and the like.

As discussed, often a formulation, such as formulation 506 illustrated in FIGS. 5 and 6, can include two or more components such as a first component 508 and a second component 510. In some embodiments, a first component can be a medicament or therapeutic component and a second component can be a diagnostic component.

In some embodiments, a formulation as described herein can include, in addition to the two or more components can include a bubble(s) 114. Bubbles can be included when the mixture is pre-filled in a syringe. In other embodiments, a formulation may outgas and create a bubble. In some embodiments, bubble(s) 114 can be a single bubble or multiple bubbles. When included, bubble(s) 114 often migrate to the highest physical location within the syringe, for example, as a result of gravity pulling the heavier formulation down and allowing the bubble(s) to migrate up. The bubbles illustrated in the Figures are merely representations of the general area where a bubble may migrate and may not show the exact location of a bubble(s). In some embodiments, the bubble(s) are merely illustrated to show that a syringe cap as described herein assists in removing bubble(s).

In an effort to prevent accumulation of visualization agents at the delivery end of a syringe, syringes can be stored in a configuration wherein this situation is avoided. FIG. 8 illustrates one such configuration. Therein, packaging 802 can be provided that allows syringe 804 to sit at angle 806 that is greater than 0. Syringe 804 is placed in a configuration wherein delivery end 808 is elevated higher than plunger end 818. In some embodiments, angle 806 is greater than about 1 degree, greater than about 2 degrees, greater than about 3 degrees, greater than about 4 degrees, greater than about 5 degrees, greater than about 6 degrees, greater than about 7 degrees, greater than about 8 degrees, greater than about 9 degrees, greater than about 10 degrees, greater than about 11 degrees, greater than about 12 degrees, greater than about 13 degrees, greater than about 14 degrees, or greater than about 15 degrees.

When syringe 804 is sitting at angle 806, second component 510 can accumulate at a location away from delivery end 808. Bubble(s) 814 can position itself at the highest location in syringe 804 adjacent to delivery end 808. In other words, when sitting at an angle, the heavier second component 510 will settle at the lowest location and bubble(s) 814 find a location at or near the highest point, here near delivery end 808.

When stored at angle 806, even if second component 510 becomes difficult to mix with first component 508, bubble(s) 814 can still be removed, or degassed, because second component 510 is not blocking delivery end 808. Thus, bubble(s) 814 can be degassed and first component 508 and second component 510 can be mixed without foaming.

Often times, however, even if packaging, such as packaging 802, is provided wherein the second component is forced toward plunger end 818 and away from delivery end 808, that packaging can still be oriented incorrectly.

In some embodiments, as illustrated in FIG. 9A, packaging 802 has been oriented on its back end 816 forcing delivery end 808 upwards and plunger end 818 downwards. Although incorrectly stored, this orientation still allows for second component 510 to accumulate at a location away from delivery end 808, for example, on top of plunger end 818. Bubble(s) 814 can still position itself at the highest location in syringe 804 adjacent to delivery end 808.

When stored on back end 816, even if second component 510 becomes difficult to mix with first component 508, bubble(s) 814 can still be removed, or degassed, because second component 510 is not blocking delivery end 808. Thus, bubble(s) 814 can be degassed and first component 508 and second component 510 mixed without foaming.

Figure 9B:
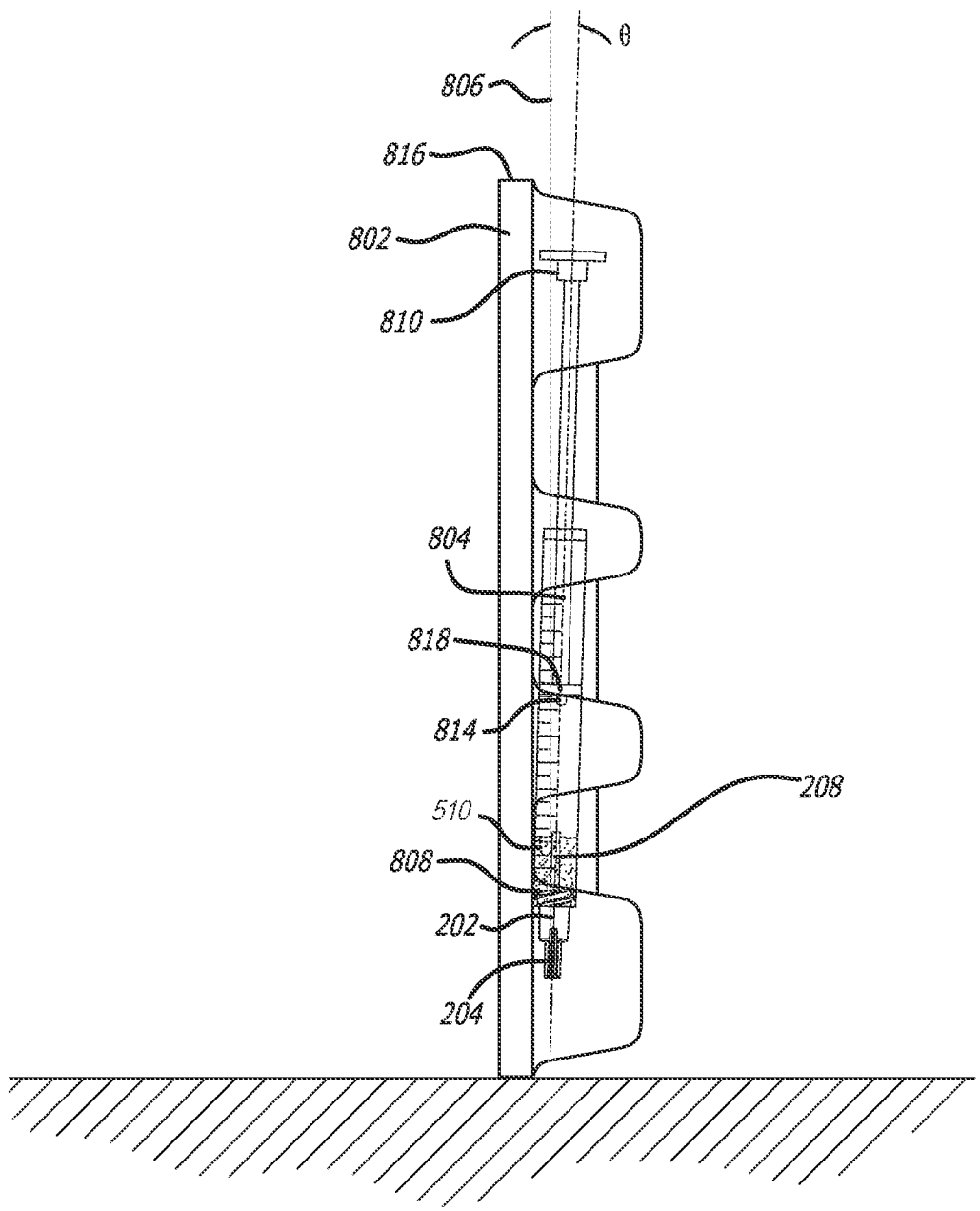
FIG. 9B illustrates syringes including syringe caps stored vertically, wrong side up, at an angle.

In other embodiments, as illustrated in FIG. 9B, packaging 802 has been oriented on its front end 820 forcing delivery end 808 downwards and plunger end 818 upwards. This orientation forces second component 510 to accumulate at delivery end 808. Bubble(s) 814 positions itself at the highest location in syringe 804 adjacent to plunger end 818.

When stored on front end 820, second component 510 may block delivery end 808 thereby preventing degassing and/or delivery of the formulation. However, if syringe cap 200 is included on delivery end 808, protruding member 208 can create an opening or tunnel through second component 510, which can allow for degassing of bubble(s) 814 before mixing.

One embodiment of using syringe cap 200 is illustrated in FIGS. 10-13. Although this description can work equally well with syringe cap 400, only syringe cap 200 will be described. FIG. 10 illustrates a syringe, syringe 1002 which has been stored in the worst possible configuration, where delivery end 1004 was pointed directly down and plunger 1016 was pointed directly up. This configuration allows second component 510 to accumulate near delivery end 1004. However, syringe 1002 is stored with syringe cap 200 installed thereon.

Second component 510 has accumulated around protruding member 208, and protruding member extends beyond the accumulation of the second component. Bubble(s) 114 was located against plunger 1016. However, once inverted, bubble(s) 114 now rests against protruding member 208 and/or second component 510, but can freely move within first component 508.

In order to prepare the composition for administration or delivery, syringe cap 200 is removed from syringe 1002. This is illustrated in FIG. 11. Therein, syringe cap 200 is unscrewed 1102 from luer threads 1008 and pulled away 1104. However, syringe cap can be removed by whatever means necessary based on its attachment configuration (e.g., pulled if friction fit).

After removal of syringe cap 200, tunnel 1006 remains through second component 510. Tunnel 1006 can provide a route for bubble(s) 114 to be removed from syringe 1002.

As illustrated in FIG. 12, after removal of syringe cap 200, a needle 1202 can be threaded onto luer threads 1008. Thereafter, bubble(s) 114 can be extruded through tunnel 1006 and needle 1202 by applying force 1204 to plunger 1016. This is often referred to as degassing.

In some embodiments, degasifying machines such as a vacuum chamber or centrifuge can be used to degas the syringe once received by the end user.

After degassing, syringe cap 200 can be threaded back onto syringe 1002. In some embodiments, needle 1202 need not be removed. At this point, syringe 1002 can be agitated 1302 to mix first component 508 and second component 510 without bubble(s) 114. This is illustrated in FIG. 13. Agitation can be in the form of shaking or vortexing. Shaking or vortexing can be accomplished using a mechanical agitating machine, such as a vortex machine, to shake the syringe until the second component is in suspension. However, in other embodiments, agitation can be using syringe-to-syringe mixing, where the composition is filled into the empty syringe with appropriate tubing, and then refilled back into the pre-filled syringe, over and over until the second component becomes suspended.

Once first component 508 and second component 510 are thoroughly mixed, the mixture 1304 can be delivered through needle 1202 or any other delivery device. In some embodiments, the delivery device can be a catheter or microcatheter.

In some embodiments, a protruding member, such as protruding member 208, can prevent second component accumulation near the delivery end of a syringe. Once this problem is avoided, a pre-filled liquid embolic syringe is then a viable alternative for an end user.

As illustrated in FIGS. 5 and 6, protruding member 208 extends through and past the settled portion of the second component, e.g., radiopaque visualization agent. The protruding member extends distally past this layer, meaning the visualization agent cannot settle past or in the section occupied by the protrusion. This helps prevent a homogenous clump from developing as there is no settled "center" of the mass due to the presence of the centered protrusion. This increases the chances that simple agitation of the syringe will separate the visualization agent from the bottom and help to re-suspend it into the embolic composition.

In some embodiments, use of a protruding member as described herein can make mixing second component with first component easier. If protruding member is removed thereby creating a tunnel through second component, then a larger surface area in contact with first component exists. Thus, when mixed, this increased surface area can enhance mixing.

In some embodiments with enhanced mixing, protruding member is removed prior to mixing. This can be accomplished by removing the herein described syringe cap and installing a conventional syringe cap without a protruding member. The composition can then be mixed.

In other embodiments with enhanced mixing, protruding member is removed prior to mixing by breaking off protruding member from a syringe cap. In such embodiments, protruding member can be provided with a perforation or other breakable or tearable portion. The composition can then be mixed.

The larger second component surface area in contact with first component can be tailored as needed for each component. Surface area can be increased by increasing the size (e.g., diameter if cylindrical) and/or length of protruding member. Surface area can be decreased by decreasing the size (e.g., diameter if cylindrical) and/or length of protruding member. In other embodiments, in addition to or alternatively, surface area can be increased by providing protruding member shapes that can increase surface area such as increased surface numbers (e.g., torx cross sections).

In one embodiment, a protruding member can be provided to create a tunnel through an accumulated second component. In this embodiment, the second component has already accumulated over the delivery end of a syringe and no protruding member has been used. Thus, the composition cannot be properly degassed. Herein, protruding member can have a sharp or pointed shape such as that illustrated in FIG. 7. The sharp or pointed portion of protruding member can be used to puncture the accumulated second component as the syringe cap is engaged with the syringe. Then, when the syringe cap is removed, a tunnel through accumulated second component can be created and mixing/vortexing can proceed as described herein.

Example 1

A physician prepares a liquid embolic composition for administration to vessels within the brain of a patient to treat arteriovenous malformations. The liquid embolic composition is provided in a prefilled syringe including a conventional syringe cap. Upon opening the syringe packaging, the physician notices that the visualization agent has accumulated over the delivery end of the syringe. The physician is unable to degas the liquid embolic composition as the instructions indicate he should. The physician proceeds to throw away the pre-filled syringe and uses another one that does not have accumulation over the delivery end that he can properly degas.

Example 2

A physician prepares a liquid embolic composition for administration to vessels within the brain of a patient. The liquid embolic composition is provided in a prefilled syringe including a syringe cap as described herein including a protruding member. Upon opening the syringe packaging, the physician notices that the visualization agent has accumulated over the delivery end of the syringe. However, the physician notices that the syringe cap includes a protruding member that traverses the accumulated mass. Based on the provided instructions, the physician removes the syringe cap and properly degasses the composition. He then reengages the syringe cap and reconstitutes the composition. The syringe is then attached to a delivery catheter and prepared for injection.

Example 3

A physician prepares a liquid embolic composition for administration to vessels within the brain of a patient to treat arteriovenous malformations. The liquid embolic composition is provided in a prefilled syringe including a conventional syringe cap. Upon opening the syringe packaging, the physician notices that the visualization agent has accumulated over the delivery end of the syringe. The physician is unable to degas the liquid embolic composition as the instructions indicate he should. Instead of throwing away the pre-filled syringe, he uses a syringe cap as described herein having a pointed protruding member to lance through the accumulated mass thereby forming a tunnel there through. Then, based on the provided instructions, the physician properly degasses the composition. He then reengages the syringe cap and reconstitutes the composition. The syringe is then attached to a delivery catheter and prepared for injection.

Example 4

A physician prepares a contrast agent composition for administration to vessels within the vasculature of a patient. The contrast agent composition is provided in a prefilled syringe including a syringe cap as described herein including a protruding member. Upon opening the syringe packaging, the physician notices that the contrast agent has accumulated over the delivery end of the syringe. However, the physician notices that the syringe cap includes a protruding member that traverses the accumulated mass. Based on the provided instructions, the physician removes the syringe cap and properly degasses the composition. He then reengages the syringe cap and reconstitutes the composition. The syringe is then attached to a delivery catheter and prepared for injection.

Example 5

A physician prepares an embolic composition that includes two prefilled syringes that must be mixed prior to delivery. A fist syringe contains a contrast agent composition and the second syringe includes a liquid embolic composition. The contrast agent syringe is provided with a syringe cap as described herein including a protruding member. Upon opening the syringe packaging, the physician notices that the contrast agent has accumulated over the delivery end of the syringe. However, the physician notices that the syringe cap includes a protruding member that traverses the accumulated mass. Based on the provided instructions, the physician removes the syringe cap and properly degasses the composition. He then reengages the syringe cap and reconstitutes the composition. The two syringes can have their contents mixed and the resulting composition is prepared for injection.

Example 6

A physician prepares an embolic composition that includes a prefilled syringe including a contrast agent and a vial including a liquid embolic composition. These two must be mixed prior to delivery. The contrast agent syringe is provided with a syringe cap as described herein including a protruding member. Upon opening the syringe packaging, the physician notices that the contrast agent has accumulated over the delivery end of the syringe. However, the physician notices that the syringe cap includes a protruding member that traverses the accumulated mass. Based on the provided instructions, the physician removes the syringe cap and properly degasses the composition. He then reengages the syringe cap and reconstitutes the composition. The contrast agent contents are delivered to the vial and mixed. The resulting composition is prepared for injection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A syringe cap including:
    a plug portion having a first end and a second end, where in an incorrect storage configuration the plug portion is connected to a delivery end of a syringe, and
    a protruding member extending from the second end of the plug portion about 2 mm to about 20 mm, wherein in the incorrect storage configuration, about 2 mm to about 20 mm of the protruding member is in direct contact with a composition including a first component and a second component housed in the syringe, and wherein the protruding member extends a length greater than a depth of the second component when accumulated.

2. The syringe cap of claim 1, wherein the protruding member extends about 5 mm.

3. The syringe cap of claim 1, wherein the protruding member extends about 10 mm.

4. The syringe cap of claim 1, wherein the protruding member has a cross-sectional shape.

5. The syringe cap of claim 4, wherein the cross-sectional shape is circular, elliptical, square, triangular, pentagonal, hexagonal, heptagonal, octagonal, torx, or star.

6. The syringe cap of claim 1, wherein the protruding member has a pointed or sharp second end.

7. The syringe cap of claim 1, further including a device capable of securing the syringe cap to the syringe.

8. The syringe cap of claim 7, wherein the device is a luer connector.

9. The syringe cap of claim 7, wherein the device is a friction connector.

10. The syringe cap of claim 1, wherein the protruding member extends about 2 mm.

11. The syringe cap of claim 1, wherein the protruding member is configured to create a tunnel through the second component when accumulated.

12. The syringe cap of claim 11, wherein the tunnel allows for degassing of the composition prior to mixing.

13. The syringe cap of claim 1, wherein the protruding member extends about 2 mm to about 5 mm.

14. The syringe cap of claim 1, wherein the protruding member extends about 2 mm to about 10 mm.

15. A system for degassing a composition in a syringe, the system comprising:
    a syringe including a connection at a delivery end;
    a syringe cap including a plug portion having a first end and a second end, wherein the plug portion is configured to attach to the connection and a protruding member extending from the second end of the plug portion;
    the composition in the syringe that includes a first component and a second component, wherein the second component accumulates when the syringe is stored, and wherein the protruding member extends a length greater than a depth of the second component when accumulated.

16. The system of claim 15, wherein the first component is a carrier, a therapeutic composition, or a combination thereof.

17. The system of claim 15, wherein the second component is a visualization agent.

18. The system of claim 17, wherein the visualization agent is configured to allow the composition to be viewed by fluoroscopy, computed tomography, or magnetic resonant imaging.

19. The system of claim 17, wherein the visualization agent includes barium, bismuth, tantalum, platinum, gold, iodine, iron oxide, gadolinium, or a combination thereof.

20. The system of claim 17, wherein the visualization agent is barium sulfate.

21. The system of claim 15, wherein the protruding member is configured to create a tunnel through the second component when accumulated.

22. A syringe system comprising:
    a syringe including a plug portion at a delivery end of the syringe, wherein the plug portion includes a protruding member extending into the syringe;
    a composition in the syringe that comprises a first component and a second component, wherein the second component accumulates when the syringe is stored;
    packaging having one or more correct storage configurations wherein the syringe is oriented such that the second component accumulates away from the delivery end; and
    wherein the protruding member extends a length greater than a depth of the second component when accumulated.

23. The syringe system of claim 22, wherein the packaging in the one or more correct storage configurations orients the syringe at an angle greater than zero relative to horizontal.

24. The syringe system of claim 22, wherein when the packaging is in at least one incorrect storage configuration which is different from the one or more correct storage configurations, the second component accumulates away from the delivery end.

* * * * *

UNITED STATES PATENT AND TRADEMARK OFFICE
CERTIFICATE OF CORRECTION

PATENT NO. : 11,911,588 B2
APPLICATION NO. : 16/986129
DATED : February 27, 2024
INVENTOR(S) : Samuel Chen and Steve Trom It is certified that error appears in the above-identified patent and that said Letters Patent is hereby corrected as shown below:

In the Claims

Claim 15, Column 16, Line 9, please replace "a syringe" with --the syringe--; and Claim 15, Column 16, Line 15, please replace "the syringe that includes" with --the syringe includes--.

Signed and Sealed this
Second Day of July, 2024

Katherine Kelly Vidal
*Director of the United States Patent and Trademark Office*